United States Patent
Cherveny et al.

(10) Patent No.: US 10,621,425 B2
(45) Date of Patent: *Apr. 14, 2020

(54) METHOD OF DETERMINING JOINT STRESS FROM SENSOR DATA

(71) Applicant: Blast Motion Inc., Carlsbad, CA (US)

(72) Inventors: Patrick Cherveny, San Marcos, CA (US); James R. Thornbrue, San Marcos, CA (US); Bhaskar Bose, Carlsbad, CA (US)

(73) Assignee: Blast Motion Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/181,955

(22) Filed: Nov. 6, 2018

(65) Prior Publication Data

US 2019/0147233 A1 May 16, 2019

Related U.S. Application Data

(63) Continuation of application No. 15/815,571, filed on Nov. 16, 2017, now Pat. No. 10,121,066.

(51) Int. Cl.
| | |
|---|---|
| *G06K 9/00* | (2006.01) |
| *A61B 5/11* | (2006.01) |
| *A61B 5/00* | (2006.01) |
| *A63B 69/00* | (2006.01) |
| *A63B 24/00* | (2006.01) |

(52) U.S. Cl.
CPC .......... *G06K 9/00342* (2013.01); *A61B 5/112* (2013.01); *A61B 5/1128* (2013.01); *A61B 5/458* (2013.01); *A61B 5/4528* (2013.01); *A61B 5/4585* (2013.01); *A63B 69/0002* (2013.01); *A61B 2503/10* (2013.01); *A61B 2562/0219* (2013.01); *A61B 2562/04* (2013.01);
(Continued)

(58) Field of Classification Search
None
See application file for complete search history.

(56) References Cited

U.S. PATENT DOCUMENTS

| | | |
|---|---|---|
| 2012/0029399 A1 | 2/2012 | Sankai |
| 2015/0138015 A1 | 5/2015 | Ishigami et al. |

(Continued)

OTHER PUBLICATIONS

International Search Report and Written Opinion issued in PCT/US2018/61435, dated Jan. 15, 2019, 7 pages.

*Primary Examiner* — Randolph I Chu
(74) *Attorney, Agent, or Firm* — Arc IP Law, PC; Joseph J. Mayo (57) ABSTRACT

A method of calculating the stress on a joint by determining when a joint angle is outside the normal range of motion for the joint. Applications include analysis of elbow joint stress for baseball pitchers, for example to mitigate the risk of injury to the ulnar collateral ligament (UCL). During a movement such as a baseball pitch, sensor data is collected to track the position, orientation, or motion of body segments; joint angles are derived from this sensor data. Joint angles are then compared to a range of motion, which may be measured for each individual. Joint stress contributions from movements that exceed the range of motion may be combined over time to calculate cumulative joint fatigue. This joint fatigue measure may for example be used for pitchers to quantify recovery periods (days off) and future workloads (such as maximum pitch counts).

10 Claims, 6 Drawing Sheets

(52) U.S. Cl.
CPC ........... *A63B 2024/0009* (2013.01); *A63B 2069/0006* (2013.01); *G06K 9/00355* (2013.01)

(56) References Cited

U.S. PATENT DOCUMENTS

| | | |
|---|---|---|
| 2015/0317801 A1 | 11/2015 | Bentley et al. |
| 2016/0008143 A1 | 1/2016 | Mahfouz |
| 2016/0045317 A1 | 2/2016 | Lang et al. |
| 2016/0140758 A1 | 5/2016 | Ooga et al. |
| 2016/0292881 A1 | 10/2016 | Bose et al. |
| 2016/0322078 A1 | 11/2016 | Bose et al. |
| 2016/0367406 A1* | 12/2016 | Barnett ............ A61B 5/48 |
| 2017/0061817 A1 | 3/2017 | May |
| 2017/0229154 A1 | 8/2017 | Bose et al. |
| 2018/0082717 A1 | 3/2018 | Bose et al. |

* cited by examiner

METHOD OF DETERMINING JOINT STRESS FROM SENSOR DATA

This application is a continuation of U.S. Utility patent application Ser. No. 15/815,571 filed 16 Nov. 2017, issued as U.S. Pat. No. 10,121,066, the specification of which is hereby incorporated herein by reference.

BACKGROUND OF THE INVENTION

Field of the Invention

One or more embodiments of the invention are related to the fields of motion analysis and biomechanics. More particularly, but not by way of limitation, one or more embodiments of the invention enable a method that determines the stress on a joint, such as an elbow for example, using sensor data.

Description of the Related Art

Human joints are subject to severe stresses that may lead to fatigue or injury. These stresses and risks are particularly acute in certain sports activities, such as baseball pitching. In baseball, for example, injury to the ulnar collateral ligament (UCL) commonly occurs in pitchers, with an increasing incidence in recent years. The UCL is located on the inside of the (medial) elbow and connects the upper arm (humerus) to a bone in the forearm (ulna). Movement patterns that simultaneously bend and twist the elbow have been shown to place the highest loads on the UCL. Dr. Frank Jobe developed a revolutionary UCL reconstructive surgical technique in 1974 that used a transplanted tendon to replace the damaged UCL. Tommy John was the first player to undergo this procedure, and Jobe's surgical technique is most commonly referred to as Tommy John Surgery (TJS). Due to the high incidence of UCL injuries in pitchers, this injury mechanism is often referred to as the Tommy John (TJ) epidemic.

These injuries result in significant time lost due to the injury itself, surgery if necessary, and the required rehab. In Major League Baseball (MLB), the dollars lost due to contracts on the disabled list (DL) and their replacement costs continue to climb year after year, jumping in 2012 due to a correlative spike in TJ related injuries. A typical rehab time frame from TJS is 12-18 months, with a statistical return to near pre-injury performance levels requiring the longer time frame of approximately 18 months. For a pitcher with a $10 million-dollar annual contract, that is a significant sunk cost. As a result, MLB and MLB teams are investing significant money into analysis of pitching injuries, with the desire to develop more predictive tools for preventing throwing injuries.

While there has been a lot of research performed on overhead throwing athletes over the past 30 years, there has not been much at all in terms of definitive injury mechanisms from these research studies. The American Sports Medicine Institute (ASMI) has performed the majority of these studies using traditional motion capture techniques. Studies to date have focused primarily on the osteokinematics of the throwing motion, which describes gross movements of skeletal bones at the joints produced by active musculotendon forces. However, joint stress is also a function of arthrokinematics, which is the very small movements of skeletal bones at the joint surface produced by passive joint properties as the joint approaches end range of motion. Passive joint stresses due to elastic structures found at a joint, including ligaments, joint capsules, and surrounding soft tissues, provide strong restoring joint moments near a joint's end range of motion. When a joint degree of freedom is isometrically held at end range of motion for some duration of time, active muscle forces are required to counteract these passive joint moments that are trying to move the joint out of the end range of motion, thereby prematurely fatiguing the same musculature that is meant to protect the joint ligaments from excessive loading during high-speed dynamic movements. Premature fatigue of the musculature of the proximal and/or distal segments may result in altered coordination and control patterns and can subject the joint ligaments to a higher percentage of total joint loading on each action (such as each throw), thereby increasing the injury risk for the athlete.

A good example of the difference between osteokinematics and arthrokinematics is to consider knee flexion/extension during sports movements. As an athlete is dynamically moving, active musculotendon forces cause the resultant knee flexion/extension that can be observed through traditional osteokinematic analysis using motion capture data. If at any point, the athlete approaches end range of motion for knee extension to the point of approaching knee hyperextension, it is at this point that we must consider arthrokinematic effects as well. As the human knee approaches full extension, a "screw-home" mechanism is employed which provides inherent knee stability to hopefully prevent catastrophic injury. If the joint continues into end range of motion, a passive joint moment is created which provides a restoring joint moment which acts to push the joint back into the normal range of motion to prevent catastrophic injury Every human joint has arthrokinematic effects. In reality, it is very difficult to accurately measure arthrokinematics, especially during high-speed athletic movements. As a result, methods known in the art to analyze joint stresses have generally not taken into account arthrokinematic effects. These effects may be modeled by taking into account active and passive joint ranges of motion, since arthrokinematic effects dominate at the end (or outside) of a joint's normal (active) range of motion as the joint transitions from an active range of motion to passive range of motion. This approach to analyzing joint stress is not known in the art. Most performance studies only consider the speed effects on joint stress. For these types of studies, the total or resultant joint stress is only used for analysis. However, when fatigue is an important consideration for dynamic performance and injury risk assessment, modeling steps that account for both active (osteokinematic) and passive (arthrokinematic) joint stress contributions are the only methodology that allows for analyses that can concurrently examine performance and injury risk.

For at least the limitations described above there is a need for a method of determining joint stress from sensor data. Embodiments of this method may for example determine the relative contributions of both active (osteokinematic) and passive (arthrokinematic) forces on total joint stress, using sensor data to determine when a joint exceeds its normal (active) range of motion.

BRIEF SUMMARY OF THE INVENTION

One or more embodiments described in the specification are related to a method of determining joint stress from sensor data. Embodiments may analyze sensor data to determine when and how long a joint is outside of its normal range of motion, thereby estimating the stress on a joint from a particular movement or the accumulated joint fatigue from a series of movements.

One or more embodiments of the invention may obtain and process sensor data that tracks the position, orientation, or motion of body parts associated with a joint. For example, to analyze the stress on an elbow joint, sensor data may track the motion of the upper arm and the forearm. Another approach for analyzing the stress on the elbow joint may be to have a sensor on the forearm near the elbow to monitor the elbow joint and a sensor on the hand or in a ball to monitor the wrist joint. A time series of joint angles for the joint may be derived from the sensor data. Joint angles may then be compared to a range of motion for the joint, or to multiple ranges of motion for a joint with multiple degrees of freedom. The range of motion for a joint may for example be measured for a specific individual; the endpoints of the normal range of motion may for example be defined as the joint angles at which the individual transitions from the active range, wherein no assistance or external force is applied to achieve a particular range of motion for the joint, (for example where one muscle group on one side of a joint is used to achieve a particular range of motion for the joint) to the passive range, wherein an external force is applied to further increase the range of motion of a joint. Intervals of time when the joint angles are outside their normal range of motion may be identified. A passive joint stress contribution may be calculated during these time intervals. This stress contribution may be calculated for example based on the amount of time that a joint angle is beyond its range of motion limits, or on the angular deviations of the joint angle from these limits.

In one or more embodiments, the joint stress contribution may be calculated as the amount of time that a joint angle is outside a corresponding range of motion. In one or more embodiments, the joint stress contribution may be based also on the joint angles themselves, for example on the degree of deviation of the angles from the range of motion limits. One or more embodiments may calculate joint stress contribution by integrating or summing one or more functions of the joint angles across a movement, or across the time intervals when the joint angles are outside the range of motion. These functions may for example represent estimates of the passive joint torque, which may for example model the arthrokinematic forces in the joint once the joint approaches or exceeds the limits of its active range of motion.

Joint stress contributions may be combined across a series of movements to calculate a joint fatigue factor. For example, one or more embodiments may apply the method of the invention to analysis of elbow joint stress for baseball pitchers. Elbow joint angles may be calculated for each pitch. The active and passive elbow stress contribution from each pitch may be determined from the amount of time the elbow was outside its normal range of motion, and from the angular magnitude of deviations from the range of motion limits. Passive joint stresses may be combined across pitches, for example during a game, or over a week or a month, to determine a cumulative elbow fatigue measurement for a pitcher. The joint fatigue measurement may be used to calculate other factors such as a recommended recovery time or a workload limit for a future time period.

In one or more embodiments, event detection may be performed by comparison of a prospective event to a characteristic signal, which may include comparison of motion capture or video capture data or both, to a range of motion values or time ordered range having different values over time, or threshold or time ordered threshold having different values over time, or any other range having an upper and lower threshold or any threshold, in order to determine if an event has occurred. The comparison of a prospective event to a characteristic signal can occur at any time and is not required to be performed immediately after a prospective event has been signified. Events such as warning or danger levels of active range may be broadcast from the motion sensor, or from a computer receiving motion capture data or video capture data or both, or shown locally on the motion sensor or a mobile device associated with the user or any combination thereof.

One or more embodiments may use inertial sensors to track motion of body parts on opposite sides of a joint. For example, for baseball pitchers, one inertial sensor may be attached to the upper arm and another inertial sensor may be attached to the forearm. Another approach for analyzing the stress on the elbow joint may be to have a sensor on the forearm near the elbow to monitor the elbow joint and a sensor on the hand or in a ball to monitor the wrist joint. Inertial sensor data may be integrated (using initial conditions for body part orientations) to obtain time series for the orientation of each body part relative to a fixed reference frame. These time series may be combined to calculate the relative orientation of one body part relative to the other, from which joint angles may be derived.

One or more embodiments may use a video camera to track body parts on opposite sides of a joint. Tracking may be done with or without visual markers attached to the body parts. Image analysis of the frames may be used to calculate joint angles.

One or more embodiments may combine inertial sensors and a video camera to track body parts and to calculate joint angles, using sensor fusion techniques to combine the inertial data and the video image analysis data into fused joint angle estimates.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION OF THE INVENTION

A method of determining joint stress from sensor data will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
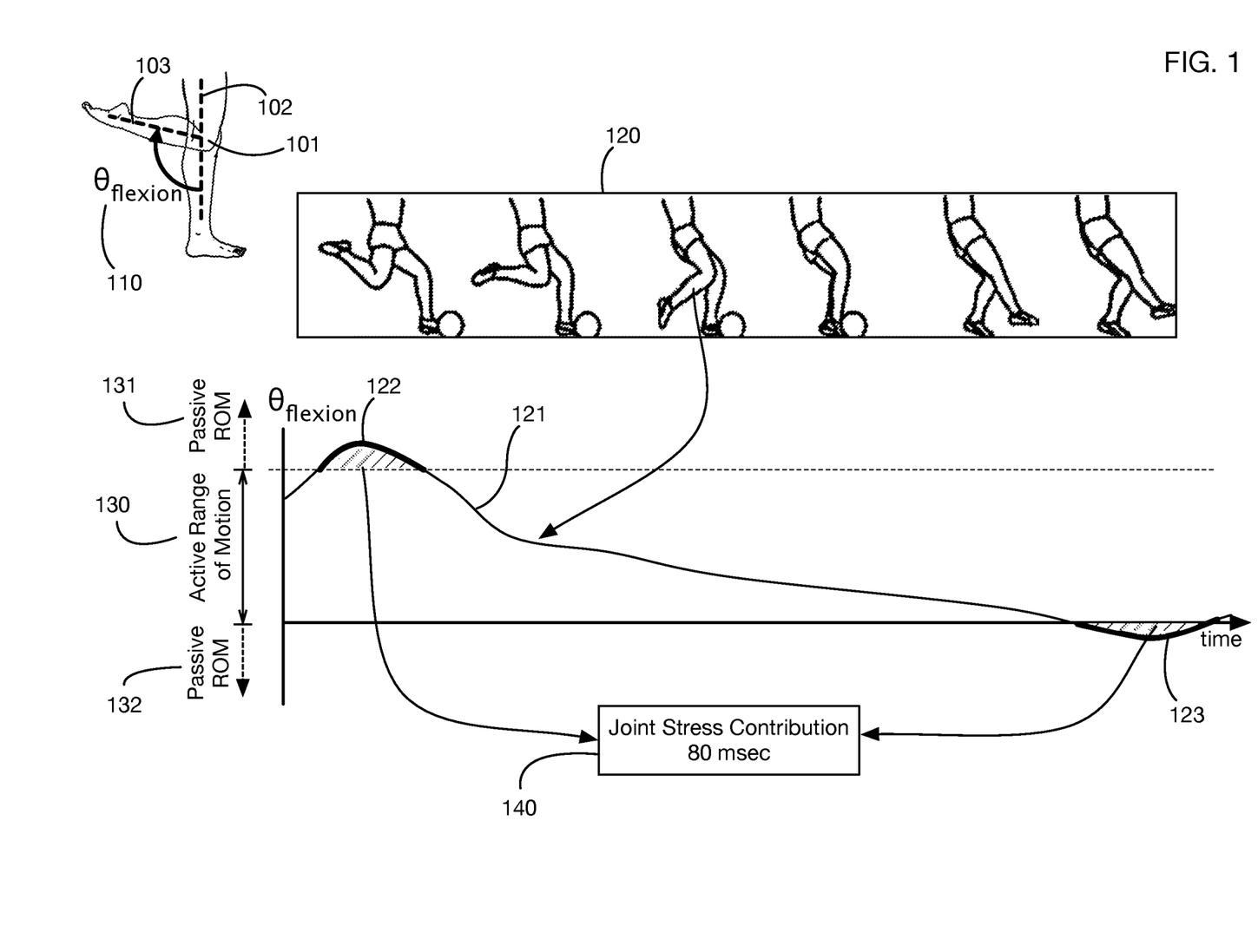
FIG. 1 shows an illustrative application of one or more embodiments of the invention: a knee joint angle is calculated during a kicking movement; and a joint stress contribution is calculated based on the amount of time the knee joint is outside its normal range of motion.

FIG. 1 shows an illustrative application of one or more embodiments of the invention. The method of the invention may be applied to analyzing any type or types of stress on any joint or joints, for any type of movement or series of movements. In the example shown in FIG. 1, the application is to analyze the passive joint stress on knee joint 101 from a kicking motion 120. Although this example shows knee joint 101, other joints including shoulders, elbows or wrists are readily measured with embodiments of the invention. This example considers a single degree of freedom the knee joint, the flexion angle 110 between the upper leg 102 and the lower leg 103. One or more embodiments of the invention may analyze motion around any number of degrees of freedom of any joint, including without limitation, joints with one, two, or three degrees of freedom. Sensor data is obtained during kicking movement 120, and is used to calculate a time series of knee joint angles 121. Data may be obtained from any type or types of sensors, including for example, without limitation, inertial sensors, magnetic sensors, ultrasonic sensors, strain gauges, video cameras, and radars. Sensor data may for example be used to track the position and orientation over time of upper leg segment 102 and lower leg segment 103, and thereby to calculate the knee flexion angle 110 over time.

Stress on the knee joint (or more generally on any body joint) is particularly high beyond the normal (active) range of motion of the joint, or as the joint angle approaches the endpoints of this normal range of motion. The "range of motion" of a joint may be divided for example into an "active" range of motion and a "passive" range of motion. The active range of motion refers to the range of joint angles that an individual can normally achieve through muscle activation until resistance is felt, or until the individual begins making adaptations in other segments. The passive range of motion refers to joint angles that can be achieved via assisted motion, for example with the help of a trainer, coach, or physical therapist. At the end points of the active range of motion of a joint, muscle-driven active torque (osteokinematics) transitions to arthrokinematics. The "normal" range of motion of a joint may for example be viewed as the active range of motion, since this is the range that an individual can achieve using normal muscle activity, without assistance. Because different individuals may have different ranges of motion for the same joint, it may be valuable to measure the range of motion for each individual, for example by determining for each individual the joint angles at which the joint transitions from its active range of motion to its passive range of motion.

Because joint torques due to arthrokinematic effects grow rapidly outside the active range of motion, one or more embodiments of the invention may determine or estimate whether, when, and for how long a body joint is outside of its normal (active) range of motion during a movement. In the example of FIG. 1, active range of motion 130 is obtained for knee joint 101 of the subject performing kicking movement 120. This range of motion applies to the knee flexion angle 110; in general, one or more embodiments may obtain or estimate ranges of motion for any degree or degrees of freedom of any joint. A range of motion for a particular joint angle is generally an interval with a lower limit and an upper limit. The range of motion may be obtained for example by measuring the active range of motion of the subject prior to the movement 120. This measurement may be performed for example using a goniometer or any other instrument or sensor. The range of motion may also be estimated from average or typical values for similar subjects; these average or typical values may be used for example in situations where is not practical to measure the range of motion for a specific individual. For example, for knee flexion angle 110 a typical active range of motion is approximately 0 degrees to 135 degrees. Because range of motion may change for a single subject over time, one or more embodiments may update the range of motion periodically using new data or new estimates. For example, the range of motion for an individual's joint may be measured immediately prior to an activity where the range of motion limits are used to calculate joint stress for that specific individual.

Beyond active range of motion 130 for joint 101, the joint enters ranges 131 and 132 that may be part of the passive range of motion for the joint. For movement 120, knee flexion angle time series 121 is outside active range of motion 130 during two periods of time: time period 122, when the knee flexes more than its normal (active) limit, and time period 123, when the knee hyperextends (with a negative flexion angle). The total duration of these two periods 122 and 123 is the joint stress contribution 140 for this movement 120. In this example, joint stress contribution 140 may represent or estimate the arthrokinematic (passive) stress that occurs in the passive range of motion zone or zones for joint angles, as opposed to joint torques generated by active osteokinematic forces within the active range of motion.

In one or more embodiments, the joint stress contribution from a movement may be calculated using any desired analysis of the joint angle time series. For example, one or more embodiments may weight passive joint stress contributions more highly when the angular deviation outside the normal (active) range of motion is greater. One or more embodiments may weight joint stress contributions differently for deviations above an upper limit of a range of motion and for deviations below a lower limit of a range of motion. One or more embodiments may calculate or estimate stresses within the active range of motion and may separately calculate or estimate stresses outside the active range of motion.

As an example, the following formula may be used for calculating a passive joint stress contribution for a joint angle time series $\theta(t)$ for a movement that occurs over time interval $[t_0, t_f]$, when the corresponding active range of motion for the joint angle is $[\theta_{min}, \theta_{max}]$ $$\text{stress} = \int_{t_0}^{t_f} \sigma(\theta(t)) dt; \qquad (1)$$

$$\text{with } \sigma(\theta) = \begin{cases} 0, & \theta \in [\theta_{min}, \theta_{max}], \\ \alpha(\theta - \theta_{max}), & \theta > \theta_{max} \\ \beta(\theta_{min} - \theta), & \theta < \theta_{min} \end{cases}$$

The weight functions $\alpha$ and $\beta$ in formula (1) above may be selected as desired to weight the angular deviations from the range of motion. For example, in the example shown in FIG. 1, the amount of time above or below the range of motion is summed; this example corresponds to $\alpha(x) \equiv 1$, $\beta(x) \equiv 1$. Other choices of these functions may include for example, without limitation: $\alpha(x) = \beta(x) = |x|$ (which weights larger angular deviations more heavily); $\alpha(x) = \beta(x) = \exp(x)$, which models a rapidly increasing stress after a joint angle hits a range of motion limit; and α(x)≡1, β(x)≡0, which considers only joint stress from going above an upper limit of the range of motion, and does not include stresses from going below a lower limit. One or more embodiments may also calculate a non-zero stress contribution for joint angles within the range of motion, for example as these angles approach the range of motion limits. These functions and formulae are illustrative; one or more embodiments may use any desired calculation or model to calculate a joint stress from joint angle time series data and from range of motion information.

Figure 1A:
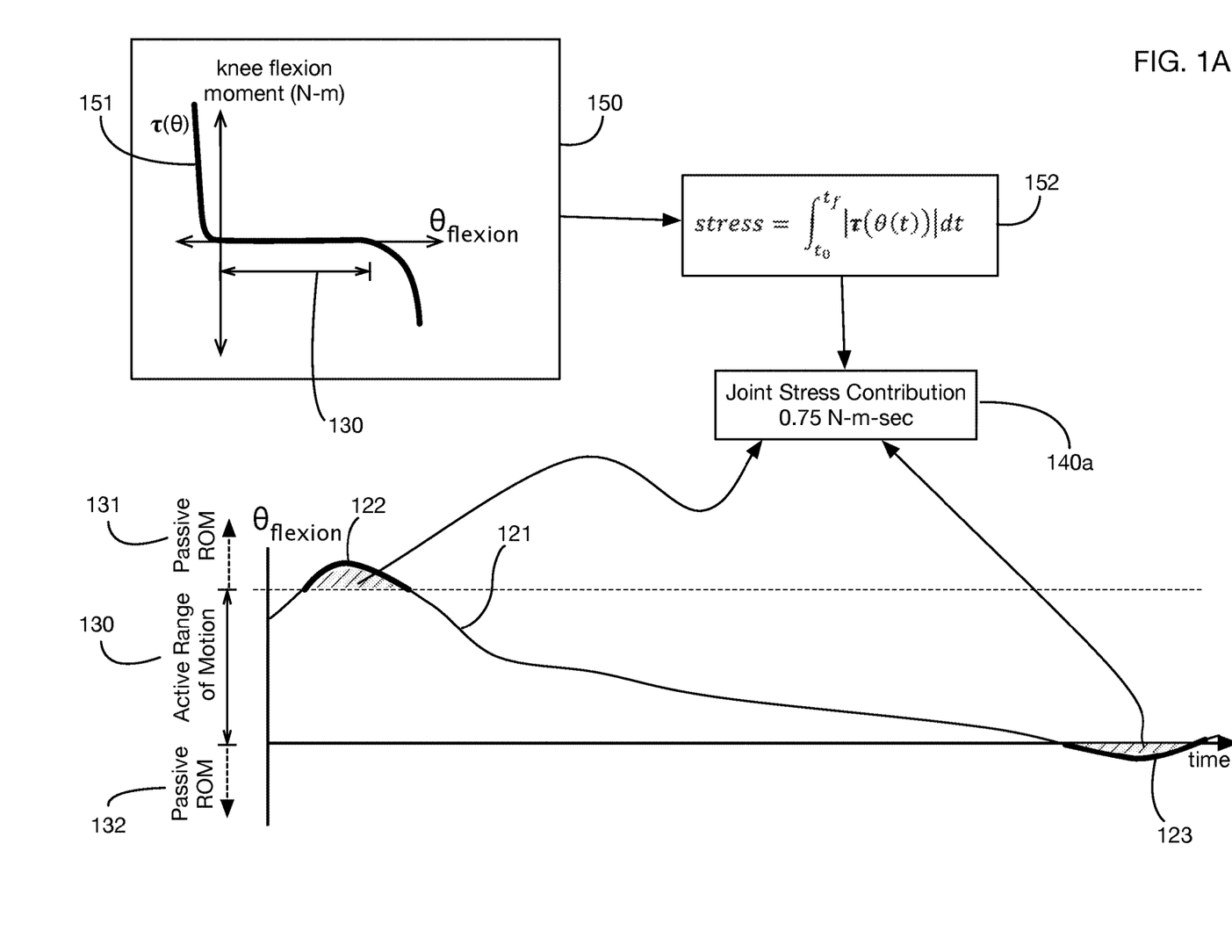
FIG. 1A shows a variation of the example of FIG. 1 that calculates joint stress using a model of passive joint torque as a function of joint angle.

FIG. 1A shows a variation of the example shown in FIG. 1. In this variation, instead of calculating joint stress as the amount of time outside the normal (active) range of motion, joint stress is calculated by integrating a model of joint torque as a function of joint angle. The illustrative joint torque model 150 provides the passive joint torque 151 as a function of the joint angle. This model may be based for example on measurement of the individual, or based on an aggregate model of typical values. For example, an individual may be tested to determine the joint angles at which this individual transitions from the active range of motion for the joint to the passive range of motion. Testing of the individual may also measure other parameters that may be used to generate a joint torque model 150 for this individual. In this illustrative model, the passive torque increases rapidly outside the range of motion 130. The passive torque may be modeled for example as a double exponential curve, with parameters determined based on range of motion limits and on the rate of growth of restoring passive torques as the joint angle approaches and then exceeds these range of motion limits. The stress may be calculated for example by integrating the torque 151 across the movement, using for example formula 152. This formula 152 is an example of formula (1) above, where the function σ(θ) in formula (1) is the magnitude of the torque 151. In this example, the joint stress contribution 140a is obtained in units of N-m-sec (resulting from integrating the torque over time). This calculation 152 is illustrative; one or more embodiments may apply any method or methods to calculate a joint stress contribution based on the time series 121 of joint angles across a motion. For example, without limitation, joint stress contribution may be based on integrated modeled torques (as in FIG. 1A), on time outside range of motion limits (as in FIG. 1), on maximum or average angular deviation above or below range of motion limits, or on any function or functions applied to joint angles (as illustrated for example in formula (1)).

Figure 2:
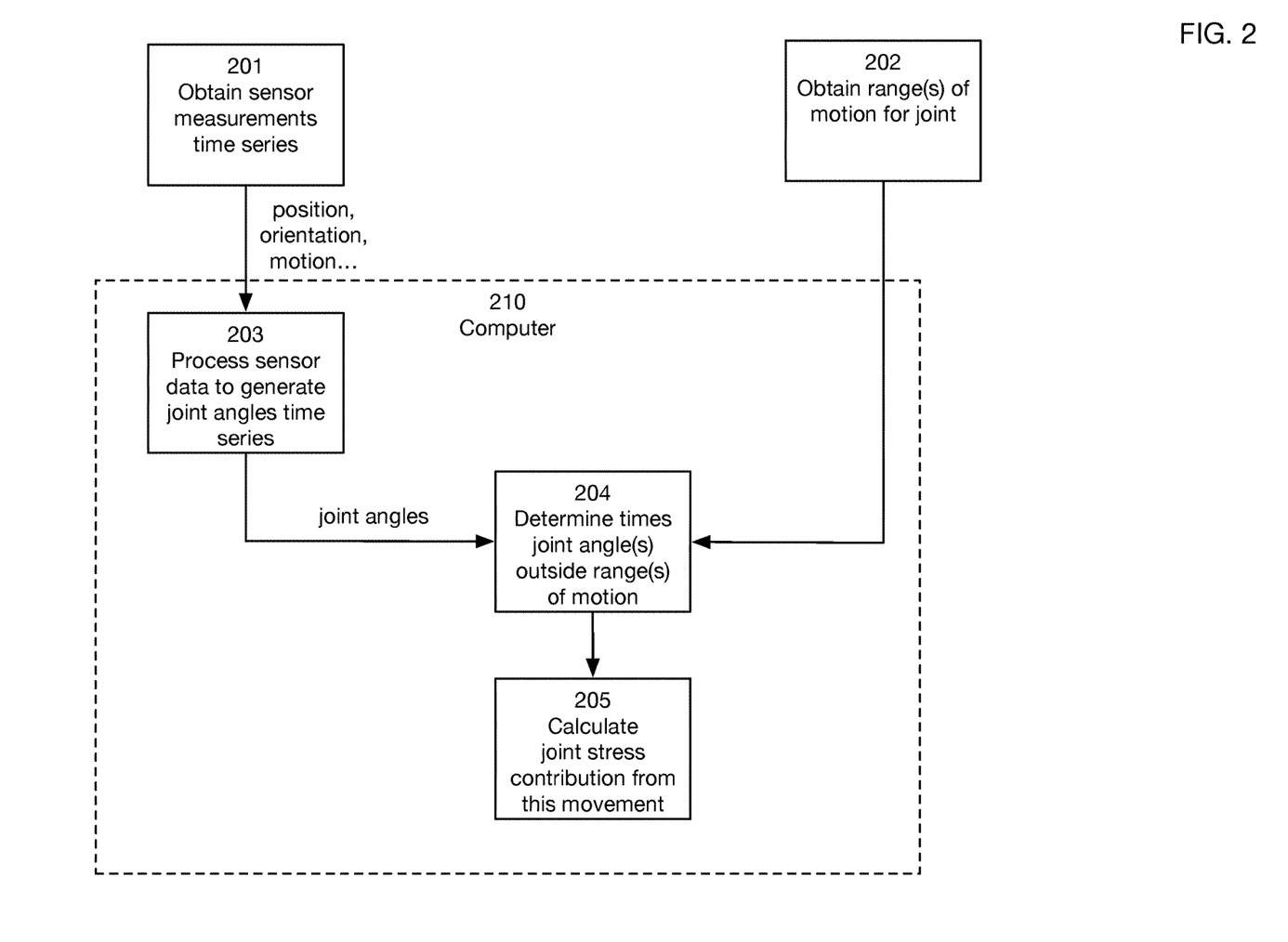
FIG. 2 shows a flowchart for one or more embodiments of the invention.

FIG. 2 shows a flowchart of the method illustrated in FIG. 1. In step 201, sensor measurements are obtained for a motion of a subject. These measurements may for example, without limitation, track the position, orientation, or motion of one or more body parts of the subject. Typically, the body parts tracked may include the body parts on either side of a joint of interest (such as the proximal (upper) and distal (lower) leg for the knee joint). In step 203, the sensor data is processed by a computer, wherein box 203 may represent a computer and step in which to specifically process the data according to embodiments of the invention, to generate a time series of joint angles for the joint or joints of interest. Alternatively, computer 210 may be utilized for any or all of the processing or calculation functionality in one or more embodiments. Computer 210 may be any type of programmable computer local or remote to the motion capture sensors in the system and is specifically programmed to perform the specific embodiments of processing detailed herein. This step may result in a single joint angle time series (as in FIG. 1), or in multiple joint angle time series for a joint with multiple degrees of freedom. In step 202, a range of motion is obtained for each joint angle of interest. This step may obtain a single range of motion for a joint with a single degree of freedom of interest (like the knee flexion angle in FIG. 1), or multiple ranges of motion if multiple degrees of freedom are analyzed. The range or ranges of motion may be measured for a specific individual; for example, the endpoints of the range of motion for a joint may be determined as the joint angles where the individual transitions from the active range of motion for the joint to the passive range of motion for the joint. A motion capture sensor may be utilized in one or more embodiments of the invention that includes any number of gyros and/or accelerometers or other sensors for example, or may be obtained via any other type of measurement device. The range or ranges of motion may correspond for example to the active range of motion for a joint, as described above. In step 204, the joint angle time series are compared to the ranges of motion, for example using a computer specifically programmed to implement embodiments of the invention so as to determine the time intervals in which the joint angles were outside of the range or ranges of motion. In step 205, a joint stress contribution calculation is made based on the deviations of the joint angles from the corresponding range or ranges of motion. In one or more embodiments, a computer specifically programmed to implement the calculation of joint stress may be utilized independently or for the computations of steps 203 or 204.

In one or more embodiments, a computer that performs any or all of the steps 201 through 205 of FIG. 2 may be any device or devices, including for example, without limitation, a microprocessor, a digital signal processor, a graphics processing unit, a coprocessor, an embedded computer, a single-board computer, a mobile device, a smartphone, a smart watch, smart glasses, a tablet computer, a laptop computer, a desktop computer, a notebook computer, a server computer, or a network of any of these devices or any other programmable device. Different devices may be used to perform different steps in the flowchart of FIG. 2, and these different devices may communicate using any type or types of networks or connections, including both wired and wireless connections. In one or more embodiments, a computer that performs any or all of these steps may be integrated into or coupled to a device or devices that also include one or more sensors.

Figure 3:
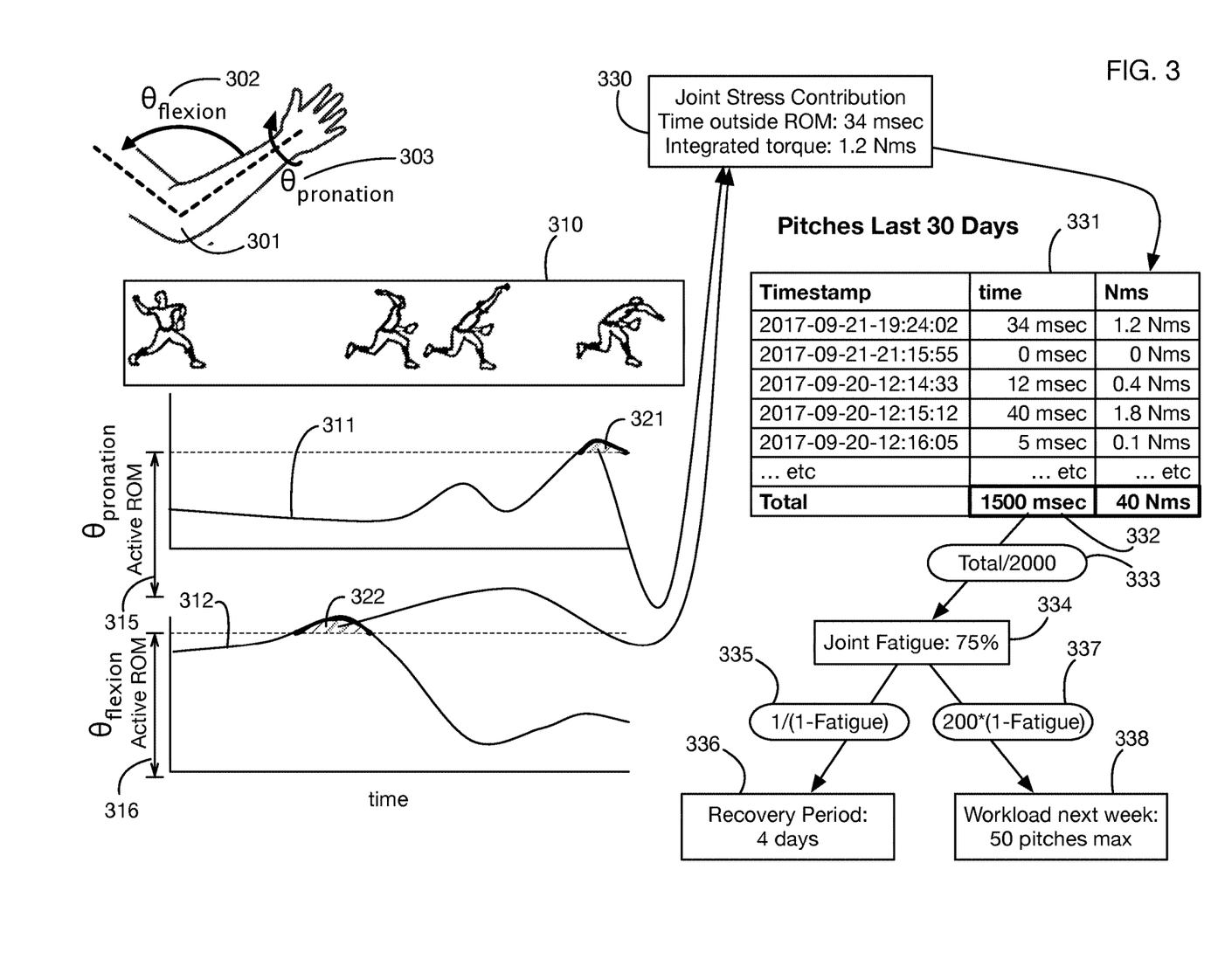
FIG. 3 illustrates application of one or more embodiments of the invention to a pitching motion, in order to analyze elbow joint stress and fatigue.

FIG. 3 shows an application of one or more embodiments of the invention to baseball pitching. An objective may be to monitor the stress on a pitcher's elbow joint 301 during a pitching motion 310. This illustrative analysis considers two degrees of freedom of elbow joint 301: flexion angle 302 (movement of the forearm towards the upper arm), and pronation angle 303 (rotation of the forearm to turn the palm inwards or outwards). Pronation angle time series 311 and flexion angle time series 312 are calculated for pitch 310, for example by processing sensor data that observes the pitcher's arm through the pitch. Range of motion 315 is obtained for the pronation angle, and range of motion 316 is obtained for the flexion angle. These ranges of motion may be obtained for example by measuring the pitcher's active range of motion. In one or more embodiments, an average or typical range of motion may be used; for example, a typical flexion range of motion may be 0 degrees to 150 degrees, and a typical pronation range of motion may be −80 degrees to +80 degrees. The pronation angle 311 is outside the corresponding pronation range of motion 315 during time period 321, and the flexion angle 312 is outside the corresponding flexion range of motion 316 during time period 322. Joint stress contribution 330 for this pitch is calculated using the methods of both FIG. 1 and FIG. 1A, resulting in the time the joint angles are outside the corresponding (active) ranges of motion, and the integrated passive torques across the movement (using for example a model of passive torques similar to model 150 in FIG. 1A.) (As described above, one or more embodiments may use other methods to calculate joint stress contribution.)

Figure 4:
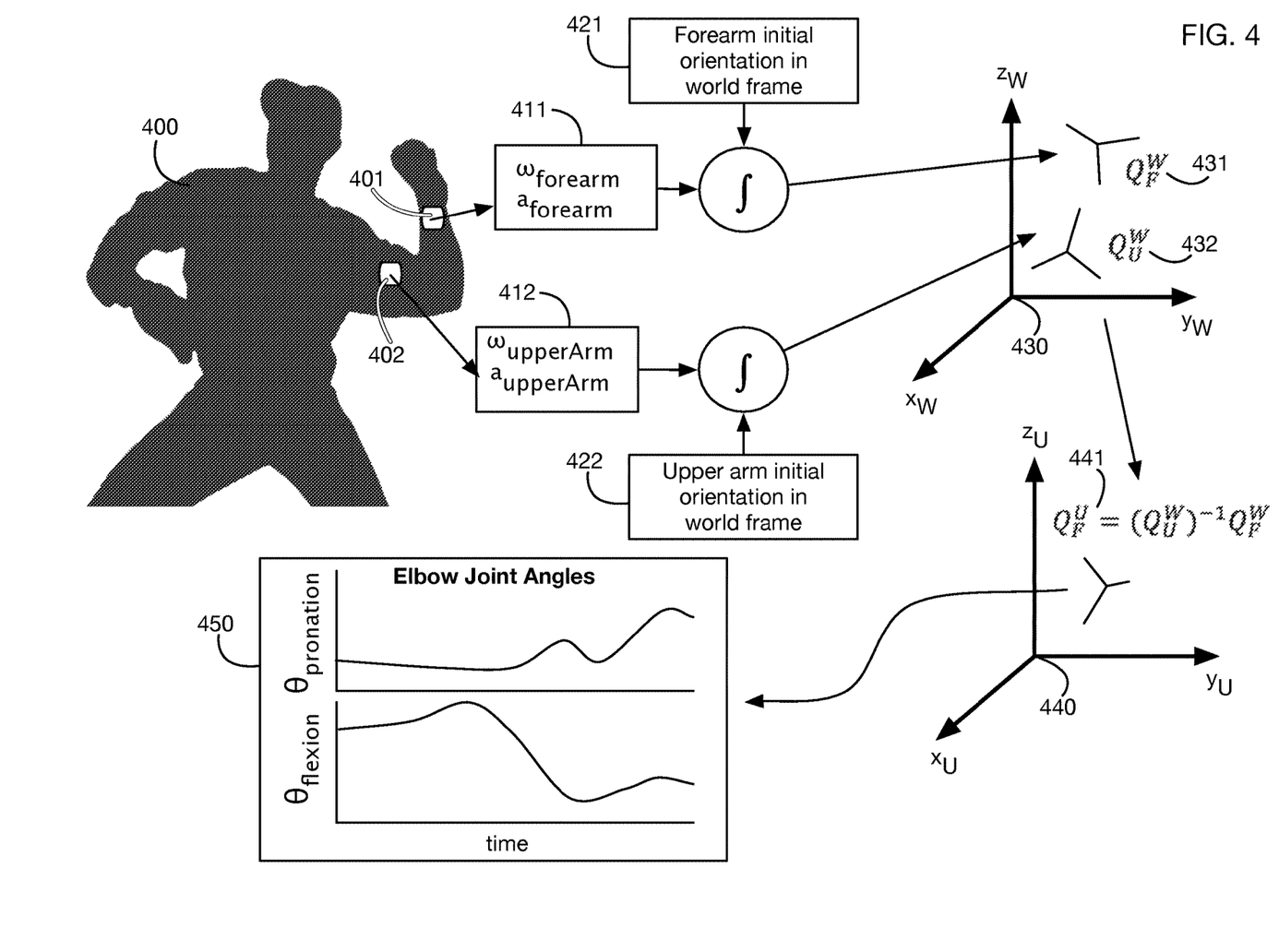
FIG. 4 illustrates a method of calculating joint angles from inertial sensor data.

FIG. 3 also illustrates extensions to the method of FIG. 2 that may be used in one or more embodiments. In addition to measuring the joint stress contribution 330 from a single movement (such as pitch 310), it may be desirable to measure a cumulative joint fatigue over a period of time. FIG. 3 illustrates a method of tracking the joint stress contributions 331 from all pitches over a time period (in this case 30 days), and calculating a total 332 for the time period. In this illustrative example, a cumulative stress contribution is calculated as a sum of the individual motion joint passive stress contributions over the time period. (This example illustrates using the total time outside the range of motion limits as an aggregate joint stress measure; the total integrated torques, or any other measures, may be used instead of or in addition to the total time.) One or more embodiments may use other methods of combining joint stress contributions over a time period, such as for example use of an exponentially weighted moving average or other weighting function. A joint fatigue index 334 is calculated from the total passive joint stress contribution 332 over the time period. In this example, the joint fatigue 334 is calculated using formula 333 as a percentage of a maximum allowable joint stress; this calculation is illustrative, and one or more embodiments may use any desired formula to calculate a joint fatigue value from the history 331 of joint stress contributions. Based on the joint fatigue, in one or more embodiments it may be desirable to calculate a recovery period 336 (such as a period of time during which the subject should rest or perform limited activities), or a maximum workload for a future time period 338. FIG. 3 shows illustrative calculations 335 and 337 that may be used to determine recovery period 336 and future workload 338, respectively. These formulae are illustrative; one or more embodiments may calculate recovery periods and workload limits using any desired methods or formulae. In one or more embodiments, any event so determined may be published to or otherwise transmitted to, or displayed on any electronic device in the system including xxx One or more embodiments may obtain sensor data from any type or types of sensors, and may calculate joint angles from this sensor data. FIG. 4 illustrates an embodiment that calculates joint angles from inertial sensor data. Pitcher 400 wears two inertial sensors—sensor 401 on the forearm, and sensor 402 on the upper arm. These sensors may for example be placed on straps, integrated into a sleeve, or integrated into clothing. The inertial sensors may for example, without limitation, include accelerometers and gyroscopes (and potentially other sensing devices as well). Angular velocity and acceleration data 411 for the forearm is obtained from sensor 401, and angular velocity and acceleration data 412 for the upper arm is obtained from sensor 402. Using inertial navigation techniques known in the art, the angular velocity and acceleration data may be integrated to provide time series for the position and orientation of the forearm and upper arm through the pitching motion. Position and orientation of each arm segment may be calculated for example relative to a world reference frame that is stationary relative to the pitcher. These integrations may also use estimates or measurements 421 and 422 of the initial orientation of each arm segment. These initial orientation estimates or measurement may for example be provided by other sensors, or the pitcher may perform a calibration procedure (such as placing the arm in a known orientation) prior to pitching. Integration of inertial data 411 and 412 with initial conditions 421 and 422 yields time series 431 and 432, which give the orientation (and potentially position) of each arm segment relative to the world frame 430. From these two time series, a relative orientation time series 441 can be calculated, for example for the orientation of the forearm relative to the upper arm. From the relative orientation time series, individual joint angles 450 may be calculated, using rotation decompositions known in the art (such as for example Euler angles or similar techniques).

In one or more embodiments, a model-based quaternion-based orientation tracking algorithm using an Extended Kalman Filter (EKF) may be used with inertial sensor data to improve accuracy of human body orientations in high-speed actions. Quaternions may be used to track rotations rather than Euler angles in order to improve computational efficiency as well as to avoid trigonometric functions and inherent singularity issues. In this model-based EKF sensor fusion algorithm, quaternion orientation estimates from the inertial sensor outputs and associated error sources (sensor bias and measurement noise) may be combined in a state vector to estimate orientation of the body segments to which they are attached. Another alternative for estimation of joint angles is to use a Kalman filter with kinematic constraints to estimate the joint axis and position. This technique offers a few advantages as it does not require a magnetometer (can be used in any location without interference), sensors can be aligned in any orientation on the attached segments, and no static calibration process or manual measurements are required. The kinematic constraints applied in this model may be used to determine the transformation from the sensor coordinate systems to the modeled joint coordinate system where the angular rotations are defined. This model may use for example only angular velocity inputs from the 3D gyroscope and linear accelerations from the 3D accelerometer attached to each segment (the proximal and distal segments to the joint of interest). A single degree of freedom joint, such as the human knee, may be modeled as a rigid mechanical hinge joint. By attaching inertial sensors to both the proximal and distal segments, one can measure the angular velocity and acceleration of both segments. With the kinematic constraint condition, the difference between the angular velocities of the proximal and distal segments (both aligned randomly on each segment and relative to one another) is mathematically found as the joint angular velocity and the rotation matrix between each sensor coordinate system. For each instant of time (sampling period), the projection of the unit axis joint vector from each sensor location to the estimated joint center when projected onto the joint plane will have the same length. From a dynamic movement data set, the angular velocity data from the proximal and distal segments can be used for example in a non-linear least squares search to determine the optimal unit axis joint vector lengths. For example, a Gauss-Newton algorithm can be used to estimate the time derivative of the joint angle of interest between the proximal and distal segments. For joints with 3 degrees of freedom (spheroid joints), the acceleration data from the accelerometers is required as well.

Figure 5:
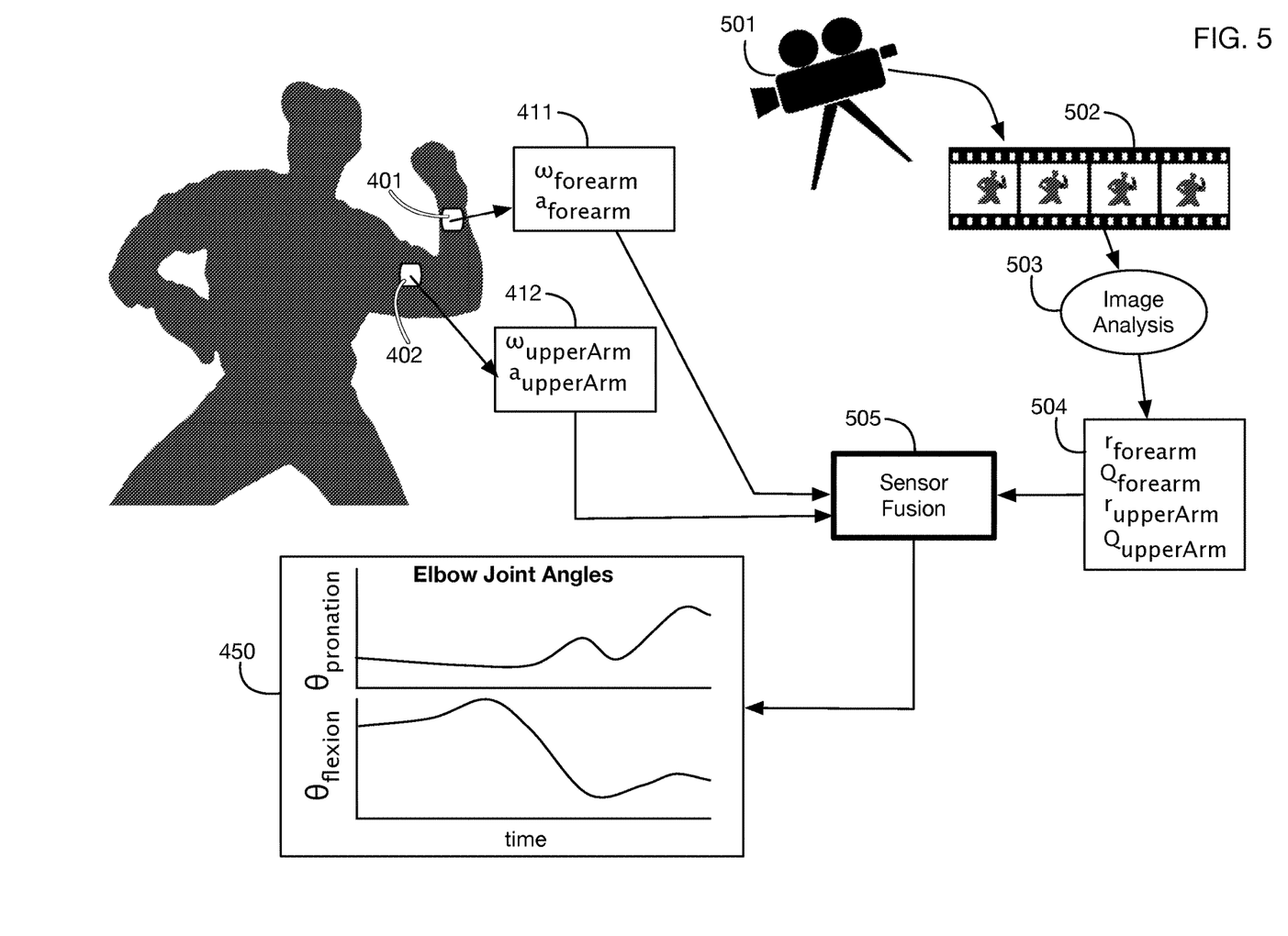
FIG. 5 illustrates a method of combining inertial sensor data and video to calculate joint angles.

One or more embodiments may combine sensor data from multiple types of sensors in order to track joint angles through a movement. FIG. 5 illustrates an example that combines a video camera 501 with the inertial sensors 401 and 402. The camera 501 may for example capture frames that track the forearm and upper arm of the pitcher through a pitch. The position and orientation 504 of each arm segment may be calculated using image analysis 503 performed on video frames 502 obtained from camera 501. In one or more embodiments, visual markers may be attached to one or more body segments to facilitate tracking of position and orientation. Image analysis 503 may for example locate the visual markers in the images of frames 502. In one or more embodiments, the visual markers may be integrated into inertial sensors; for example, sensors 401 and 402 may incorporate distinctive visual patterns or other elements to facilitate tracking of the sensors by the video camera. Visual markers may also incorporate reflective elements or specialized materials, such as an infrared reflective material. In one or more embodiments, visual makers may actively emit light to facilitate tracking.

This position and orientation information 504 may be fused with inertial data 411 and 412 using any desired sensor fusion technique 505, resulting in joint angle time series 450. Sensor fusion techniques may include for example, without limitation, Kalman filters or extended Kalman filters. In particular, in one or more embodiments position and orientation data 504 from image analysis 503 may be used as initial conditions 421 and 422 for inertial integration as described with respect to FIG. 4.

Estimating joint angles using sensor fusion of inertial data and video data may for example be used with markerless mocap (motion capture) systems, which offer advantages of markerless data capture, but suffer from known accuracy issues in long-axis rotation measurements. A known angular velocity value, or some average and range, from an inertial sensor helps to constrain the 3D marker trajectory from the optical system. For example, forearm pronation/supination requires estimating the range that points on the medial (middle) and lateral (outside) of the wrist move during an action. Due to the close proximity of these points, small positional errors can result in significant angular rotation errors. Research has demonstrated that errors of 10-15 degrees in pronation can be found in markerless mocap systems. During the dynamic throwing motion, this can occur in a very small time sample of 10 milliseconds. This could result in an error of 1,500 degrees per second. Known angular velocity time series for a subject could be used to constrain the markerless mocap data to match these expected angular velocity envelopes when there is uncertainty in the measured positional data from the markerless mocap system.

While the invention herein disclosed has been described by means of specific embodiments and applications thereof, numerous modifications and variations could be made thereto by those skilled in the art without departing from the scope of the invention set forth in the claims.

What is claimed is:

1. A method of determining joint stress from sensor data comprising:
   obtaining a time series of sensor measurements from one or more sensors comprising
      a first sensor coupled to a first body part or oriented to track said first body part, wherein said first sensor comprises one or more of an inertial sensor, a magnetic sensor, an ultrasonic sensor, a strain gauge, a video camera, a radar; and,
      a second sensor coupled to a second body part or oriented to track said second body part, wherein said second sensor comprises one or more of an inertial sensor, a magnetic sensor, an ultrasonic sensor, a strain gauge, a video camera, a radar;
   measuring
      one or more of position, orientation, or motion of said first body part of a subject using said first sensor, and
      one or more of position, orientation, or motion of said second body part of said subject using said second sensor;
   wherein
      said first body part and said second body part are coupled to a body joint of said subject; and,
      said first body part and said second body part lie on opposite sides of said body joint;
   processing said time series of sensor measurements to generate one or more joint angle time series for said body joint, wherein
      each joint angle time series corresponds to a joint angle of said body joint; and,
      each said joint angle of said body joint corresponds to a rotational degree of freedom of said body joint;
   obtaining one or more active ranges of motion for said body joint, wherein
      each active range of motion of said one or more active ranges of motion corresponds to said joint angle of said body joint; and,
      said each active range of motion of said one or more active ranges of motion comprises an interval of joint angles that are within said active range of motion;
   determining one or more passive range of motion time intervals, each corresponding to a time period when one or more of said one or more joint angle time series has a joint angle value that is outside a corresponding active range of motion associated with said joint angle;
   calculating a joint stress contribution using a computer during said one or more passive range of motion time intervals;
   combining said joint stress contribution across a plurality of movements by said subject during a period of time to calculate a joint fatigue;
   publishing or transmitting or displaying, or any combination thereof, using a computer, said joint fatigue.

2. The method of claim 1, wherein said calculating said joint stress contribution during said one or more passive range of motion time intervals comprises:
   calculating an amount of time within said one or more passive range of motion time intervals.

3. The method of claim 1, wherein said calculating said joint stress contribution during said one or more passive range of motion time intervals comprises:
   integrating or summing one or more functions of said joint angle value across said one or more passive range of motion time intervals.

4. The method of claim 3, wherein said one or more functions of said joint angle comprise one or more estimates of a passive joint torque as a function of said joint angle value.

5. The method of claim 1, wherein
   said subject is a pitcher;
   said body joint is an elbow of said pitcher; and,
   said plurality of movements comprise pitches by said pitcher.

6. The method of claim 1, further comprising:
   obtaining or calculating
      an initial orientation of said first body part relative to a reference frame; and, an initial orientation of said second body part relative to said reference frame.

7. The method of claim 6, wherein said processing said time series of sensor measurements to generate said one or more joint angle time series for said body joint comprises:
   integrating said time series of sensor measurements using said initial orientation of said first body part and said initial orientation of said second body part as initial conditions, to generate
      a time series of orientation of said first body part relative to said reference frame, and
      a time series of orientation of said second body part relative to said reference frame;
   calculating a time series of relative orientation of said second body part relative to said first body part from said time series of orientation of said first body part relative to said reference frame and said time series of orientation of said second body part relative to said reference frame;
   calculating said one or more joint angle time series for said body joint from said time series of relative orientation of said second body part relative to said first body part.

8. The method of claim 1, wherein said one or more sensors further comprise
   at least one video camera configured to capture a plurality of frames, each frame of said plurality of frames containing an image of one or both of said first body part and said second body part.

9. The method of claim 8, further comprising:
coupling a first visual marker to said first body part; and,
coupling a second visual marker to said second body part;
wherein said plurality of frames contains one or more images of one or both of said first visual marker and said second visual marker.

10. The method of claim 8, further comprising:
using a sensor fusion algorithm to combine a time series of position and orientation information calculated from said plurality of frames with motion data from a first inertial sensor coupled to said first body part and a second inertial sensor coupled to said second body part, to generate a combined estimate of said one or more joint angle time series.

* * * * *